United States Patent
Baum

(10) Patent No.: US 6,344,079 B1
(45) Date of Patent: *Feb. 5, 2002

(54) ALKANE AND POLYAMINE SOLVENT COMPOSITIONS FOR LIQUID DELIVERY CHEMICAL VAPOR DEPOSITION

(75) Inventor: Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/454,954

(22) Filed: Dec. 3, 1999

Related U.S. Application Data

(63) Continuation-in-part of application No. 09/185,374, filed on Nov. 3, 1998, now Pat. No. 6,214,105, and a continuation-in-part of application No. 09/224,614, filed on Dec. 31, 1998, now Pat. No. 6,111,124, which is a continuation of application No. 08/975,372, filed on Nov. 20, 1997, now Pat. No. 5,916,359, which is a continuation-in-part of application No. 08/960,915, filed on Oct. 30, 1997, now Pat. No. 5,859,274, which is a continuation-in-part of application No. 08/484,654, filed on Jun. 7, 1995, now Pat. No. 6,110,529, which is a continuation-in-part of application No. 08/414,504, filed on Mar. 31, 1995, now Pat. No. 5,820,664.

(51) Int. Cl.⁷ .............................. C09K 3/00; C23C 16/40
(52) U.S. Cl. .............................. 106/287.18; 106/287.19; 252/182.12; 423/DIG. 14; 427/248.1; 501/135; 505/447; 505/512; 556/79
(58) Field of Search .................. 44/432, 362; 106/1.25, 106/287.19, 287.18; 252/182.12; 427/248.1; 501/135, 137; 505/447, 512; 556/40, 79; 585/2, 3; 423/DIG. 14

(56) References Cited

U.S. PATENT DOCUMENTS

| | | | | |
|---|---|---|---|---|
| 4,147,556 A | * | 4/1979 | Donley ................... | 106/287.18 |
| 5,165,960 A | * | 11/1992 | Platts ..................... | 427/166 |
| 5,376,409 A | * | 12/1994 | Kaloyeros et al. ....... | 427/248.1 |
| 5,451,434 A | * | 9/1995 | Doellein ................. | 505/447 X |
| 5,453,494 A | * | 9/1995 | Kirlin et al. ............. | 505/512 X |
| 5,504,195 A | * | 4/1996 | Leedham et al. ......... | 534/15 |
| 5,593,464 A | * | 1/1997 | Cook et al. .............. | 44/362 |
| 5,820,664 A | * | 10/1998 | Gardiner et al. ......... | 106/287.17 |
| 5,833,745 A | * | 11/1998 | Atsuki et al. ............ | 106/287.18 |
| 5,916,359 A | * | 6/1999 | Baum et al. ............. | 106/287.18 |

FOREIGN PATENT DOCUMENTS

| | | | | |
|---|---|---|---|---|
| GB | 258641 | * | 9/1926 | ................... 556/79 |
| SU | 530875 | * | 1/1977 | ..................... 585/3 |

OTHER PUBLICATIONS

G.S. Brady: "Materials Handbook—An Encyclopedia for Purchasing Agents, Engineers, Executives, and Foremen", Ninth Edition McGraw–Hill Book Co.,Inc., New York, p. 500, 1963.*

* cited by examiner

*Primary Examiner*—Richard D. Lovering
(74) *Attorney, Agent, or Firm*—Oliver A. Zitzmann; Margaret Chappuis; Robert McLauchlan

(57) ABSTRACT

A solvent composition for liquid delivery chemical vapor deposition of metal organic precursors, to form metal-containing films such as $SrBi_2Ta_2O_9$ (SBT) films for memory devices. An SBT film may be formed using precursors such as $Sr(thd)_2(pmdeta)$, $Ta(OiPr)_4(thd)$ and $Bi(thd)_3(pmdeta)$ which are dissolved in a solvent medium comprising one or more alkanes. Specific alkane solvent compositions may advantageously used for MOCVD of metal organic compound(s) such as β-diketonate compounds or complexes, compound(s) including alkoxide ligands, and compound(s) including alkyl and/or aryl groups at their outer (molecular) surface, or compound(s) including other ligand coordination species and specific metal constituents.

26 Claims, 2 Drawing Sheets

ALKANE AND POLYAMINE SOLVENT COMPOSITIONS FOR LIQUID DELIVERY CHEMICAL VAPOR DEPOSITION

CROSS-REFERENCE TO RELATED APPLICATIONS

This is a continuation in part of U.S. patent application Ser. No. 09/185,374 filed Nov. 3, 1998, now U.S. Pat. No. 6,214,105, which is a continuation of application Ser. No. 08/975,372 filed Nov. 20, 1997, now U.S. Pat. No. 5,916,359, which is a continuation in part of U.S. patent application Ser. No. 08/484,654 filed Jun. 7, 1995, now U.S. Pat. No. 6,110,529, which is a continuation in part of U.S. patent application Ser. No. 08/414,504 filed Mar. 31, 1995, now U.S. Pat. No. 5,820,664.

This is also a continuation in part of U.S. patent application Ser. No. 09/224,614 filed Dec. 31, 1998, now U.S. Pat. No. 6,111,124, which is a continuation in part of U.S. patent application Ser. No. 08/960,915 filed Oct. 30, 1997, now U.S. Pat. No. 5,859,274.

BACKGROUND OF THE INVENTION

1. Field of the Invention

The present invention relates to a solvent composition useful for liquid delivery chemical vapor deposition of metal organic precursors including metal (beta-diketonato) precursors.

2. Description of the Related Art

In the liquid delivery method of carrying out chemical vapor deposition (CVD) processes, a solid precursor is dissolved in an appropriate solvent mixture or a liquid-phase precursor is vaporized and the resulting precursor vapor, typically mixed with a carrier gas (such as argon, heliun or nitrogen) is transported to the chemical vapor deposition reactor. In the reactor, the precursor vapor stream is contacted with a heated substrate to effect decomposition and deposition of a desired component or components from the solution and/or vapor phase on the substrate surface.

In such liquid delivery CVD process, a wide variety of solvents have been employed for dissolution or suspension of precursor species, with the liquid solution or suspension being vaporized by various techniques, including flash vaporization on a heated element onto which the liquid containing the precursor is discharged, to volatilize the solvent and precursor species.

In many instances, where a variety of precursors are employed to form a multi-component deposited film in the CVD process, it is desirable to utilize a single solvent medium for the respective precursor species, for ease of operation and simplicity of the process system, thereby avoiding any deleterious solvent-solvent interactions which may occur if different solvent media are utilized for different precursor species. Further, it is desirable that solvent compositions when used for multiple species not interact with the precursor or metal-containing molecules to form unstable chemical solutions, since such instability renders the overall composition unsuitable for liquid delivery.

In a specific field in which the present invention has applicability, ferroelectric ceramic materials based on bismuth oxide are promising materials for use in non-volatile memories. Promising candidates derive from the group of Aurivillius phase compounds having the general formula:

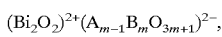

wherein A=$Bi^{3+}$, $L^{3+}$, $L^{2+}$, $Ca^{2+}$, $Sr^{2+}$, $Ba^{2+}$, $Pb^{2+}$, $Na^+$, B=$Fe^{3+}$, $Al^{3+}$, $Sc^{3+}$, $Y^{3+}$, $L^{4+}$, $Ti^{4+}$, $Nb^{5+}$, $Ta^{5+}$, $W^{6+}$, $Mo^{6+}$, with L=metal from the lanthanide series, such as $Ce^{4+}$, $La^{3+}$, $Pr^{3+}$, $Ho^{3+}$, $Eu^{2+}$, $Yb^{2+}$, etc. and m=1, 2, 3, 4, 5.

Among materials of the foregoing type, $SrBi_2Ta_2O_9$ (SBT) and $Bi_4Ti_3O_{12}$ find widespread interest for integration in ferroelectric random access memories (FeRAMs) and in smart cards.

In chemical vapor deposition processes for SBT, the use of precursors such as $Sr(thd)_2(tetraglyme)$, $Ta(OiPr)_4(thd)$ and triphenyl bismuth, dissolved in a solvent medium such as tetrahydrofuran:isopropanol:tetraglyme in a volumetric ratio of 8:2:1 produced the result that $Bi_2O_3$ deposition was difficult to control. Efforts to resolve such difficulties included replacement of the triphenyl bismuth precursor with mononuclear $Bi(thd)_3$ with the latter precursor showing a reliable and reproducible $Bi_2O_3$ deposition rate. Unfortunately, however, in the vaporizer the $Bi(thd)_3$ precursor caused the formation of black bismuth-rich residues, indicating premature decomposition was taking place during vaporization and transport. Such premature decomposition allowed only ten operational runs to be conducted with the $Bi(thd)_3$ precursor until the vaporizer required maintenance to remove unwanted deposits.

Chemical considerations associated with the foregoing adverse decomposition indicated the solvent system was one source of the problem. It appeared that in the presence of isopropanol dinuclear $Bi(thd)_3$ precursor was formed and at the elevated temperature conditions of the vaporizer (190° C.) the precursor was reduced to Bi metal producing the black residue. Concurrently, it is expected that the IPA is oxidized during this decomposition (redox) reaction.

Accordingly, an improved solvent system is desired for such deposition process for the formation of SBT films. Such a solvent system faces a number of problems. The solubility of the precursors in the solvent medium must be sufficiently high to provide adequate precursor delivery rates in the vaporizer. Moreover, there should not be a precipitation of material over a period of time due to any slight oversaturation incurred during preparation of the source reagent compositions, or caused by a ligand exchange among the different precursor species.

It therefore is the object of the present invention to provide a novel solvent composition having broad utility for CVD precursors, such as those comprising metal organic compositions with β-diketonate ligands.

Other objects and advantages of the present invention will be more fully apparent from the ensuing disclosure and appended claims.

SUMMARY OF THE INVENTION

The present invention relates in one aspect to a solvent composition for liquid delivery chemical vapor deposition of metal organic precursors.

One composition of the invention comprises a mixture of solvent species A, B and C in the proportion A:B:C, wherein A is from about 1 to about 10 parts by volume, B is from about 0 to about 6 parts by volume, and C is present from 1 up to about 4 parts by volume, wherein such parts by volume are based on the total volume of the mixture, and wherein A is a $C_6$–$C_8$ alkane, B is a $C_8$–$C_{12}$ alkane, A and B are different from one another, and C is a glyme-based solvent (glyme, diglyme, triglyme, tetraglyme, etc.), a polyamine, and/or other suitable Lewis base ligand.

As used hereinafter, a Lewis base ligand is defined as a molecule that can donate an electron pair.

In one specific and preferred aspect, the solvent composition may comprise (A) octane, (B) decane, and (C) an amine, a diamine or a polyamine, in approximately 5:4:1 proportion (of A:B:C) by volume.

In another specific and preferred aspect, the solvent composition may comprise (A) octane and (C) an amine, a diamine or a polyamine, in approximately 9:1 proportion (of A:C) by volume.

Concerning preferred amine, diamine and polyamine species for component C in the composition of the solvent composition, preferred amine species include trialkylamine, preferred diamines include tetraalkyl ethylene diamine, and preferred polyamine species include N,N,N',N'-tetramethylethylenediamine, N,N,N',N",N"-pentamethyldiethylenetriamine, and N,N, N',N",N'",N'"-hexamethyltriethylenetetramine.

In another aspect, the present invention relates to a precursor composition for liquid delivery chemical vapor deposition, comprising at least one metal organic precursor component in a solvent composition comprising a mixture of solvent species A, B and C in the proportion A:B:C wherein A is from about 1 to about 10 parts by volume, B is from about 0 to about 6 parts by volume, and C is present from 1 up to about 4 parts by volume, wherein such parts by volume are based on the total volume of the mixture, and wherein A is a $C_6$–$C_8$ alkane, B is a $C_8$–$C_{12}$ alkane, A and B are different from one another, and C is a Lewis: base ligand selected from the group consisting of glyme-based solvents (glyme, diglyme, triglyme, tetraglyme, etc.) ethers, amines, diamines and polyamines aryls and aryl amines. The metal organic precursor in such composition may for example comprise one or more metal β-diketonate(s) and/or adduct(s) thereof.

In another aspect, the present invention relates to a precursor composition for liquid delivery chemical vapor deposition, comprising a bismuth Lewis base adduct precursor having the formula Bi(β-diketonate)$_3$(L)$_m$, dissolved in a solvent composition comprising one or more alkanes and a Lewis base ligand, wherein L is a Lewis base ligand and m is a value between ½ and 5 and the Lewis base ligand of the precursor component and the Lewis base ligand of the solvent composition are the same.

In another aspect, the present invention relates to a precursor composition for liquid delivery chemical vapor deposition, comprising the metal organic precursor components Sr(β-diketonate)$_2$(L)$_m$, Ta(alkoxide)$_4$(β-diketonate) and Bi(β-diketonate)$_3$(L)$_m$, dissolved in a solvent composition comprising one or more alkanes and a Lewis base ligand, wherein L is a Lewis base ligand and m is a value between ½ and 5 and the Lewis base ligand of the precursor component and the Lewis base ligand of the solvent composition are the same.

In a preferred aspect, the present invention relates to a precursor composition for liquid delivery chemical vapor deposition, comprising Sr(thd)$_2$(pmdeta), Ta(OiPr)$_4$(thd) and Bi(thd)$_3$(pmdeta), in a solvent composition comprising (A) octane, (B) decane, and (C) pmdeta, in approximately 5:4:1 proportion (of A:B:C) by volume.

Another aspect of the invention relates to a liquid delivery MOCVD method of forming a metal-containing film on a substrate including the steps of vaporizing a precursor composition to form a precursor vapor, and contacting the precursor vapor with the substrate to deposit said metal-containing film, wherein the precursor composition includes a solvent medium comprising one or more alkanes, having dissolved therein one or more compatible metal organic compound(s) selected from the group consisting of (i) β-diketonate compound(s) and/or adducts thereof (ii) compound(s) including alkoxide ligands, and (iii) compound(s) including alkyl and/or aryl groups.

A further aspect of the invention relates to a process for forming a bismuth containing film on a substrate, in applications such as the formation of ferroelectric microelectronic device structures, comprising a bismuth Lewis base adduct precursor having the formula Bi(β-diketonate)$_3$(L)$_m$, dissolved in a solvent composition comprising one or more alkanes and a Lewis base ligand, wherein L is a Lewis base ligand and m is a value between ½ and 5 and the Lewis base ligand of the precursor component and the Lewis base ligand of the solvent composition are the same.

In a still further aspect, the invention relates to a process for forming a film of SrBi$_2$Ta$_2$O$_9$ (SBT) on a substrate, in applications such as the formation of ferroelectric microelectronic device structures, comprising the precursors Sr(β-diketonate)$_2$(L)$_m$, Ta(alkoxide)$_4$(β-diketonate) and Bi(β-diketonate)$_3$(L)$_m$ in a solvent composition comprising one or more alkanes and a Lewis base ligand, wherein L is a Lewis base ligand and m is a value between ½ and 5 and the Lewis base ligand of the precursor component and the Lewis base ligand of the solvent composition are the same.

In a preferred aspect, the invention relates to a process for forming a film of SrBi$_2$Ta$_2$O$_9$ (SBT) on a substrate, in applications such as the formation of ferroelectric microelectronic device structures, comprising the precursors Sr(thd)$_2$(pmdeta), Ta(OiPr)$_4$(thd) and Bi(thd)$_3$(pMdeta), in a solvent composition comprising (A) octane, (B) decane, and (C) pmdeta approximately 5:4:1 proportion (of A:B:C) by volume.

In another preferred aspect, the invention relates to a process for forming a film of SrBi$_2$Ta$_2$O$_9$ (SBT) on a substrate, in applications such as the formation of ferroelectric microelectronic device structures, comprising the precursors Sr(thd)$_2$(pmdeta), Ta(OiPr)$_4$(thd) and Bi(thd)$_3$(pmdeta), in a solvent composition comprising (A) octane, and (C) pmdeta, in approximately 9:1 proportion (of A:C) by volume.

In another aspect, the invention relates to a process for forming a film of SrBi$_2$Ta$_2$O$_9$ (SBT) on a substrate, in applications such as the formation of ferroelectric microelectronic device structures, wherein the precursors Sr(thd)$_2$(tetraglyme), Ta(OiPr)$_4$(thd) and Bi(thd)$_3$ are employed in a solvent medium comprising one or more alkanes.

A still further aspect of the invention relates to a precursor composition for MOCVD of a metal-containing film on a substrate, wherein the precursor composition includes a solvent medium comprising one or more alkanes and/or arenes, having dissolved therein one or more compatible metal organic compound(s). Such compound(s) may for example be β-diketonate compounds or complexes and/or adducts thereof, compound(s) including alkoxide ligands, compound(s) including alkyl and/or aryl groups at their outer (molecular) surface, or compound(s) including other ligand coordination species (i.e., Lewis base ligands) and specific metal constituents.

In one embodiment, such compound(s) may be selected from the group consisting of Sr(thd)$_2$(tetraglyme), Sr(thd)$_2$(Polyamine), Ba(thd)$_2$(tetraglyme), Ba(thd)$_2$(Polyamine), Ta(OiPr)$_4$(thd), Ti(OiPr)$_2$(thd)$_2$, Zr(OiPr)$_2$(thd)$_2$, Bi(thd)$_3$, Bi(thd)$_3$(polyamine), Pb(thd)$_2$, Pb(thd)$_2$(tmeda), Pb(thd)$_2$(pmdeta), Pt(thd)$_2$, Pt(hfac)$_2$, (methylcyclopentadienyl)Pt (Me)$_3$, (MeCN)$_2$PtMe$_2$, Pd(allyl)$_2$, Pd(hfac)$_2$, Me$_2$Au(hfac), MeAu(PMe$_3$), Cu(hfac)$_2$, (COD)Cu(hfac), (DMCOD)Cu (hfac), (MHY)Cu(hfac), (Me$_3$P)CuO$^t$Bu, Ta(OR)$_5$, and Ti(OR)$_4$, wherein R=C$_1$–C$_8$ alkyl (branched or straight chain).

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
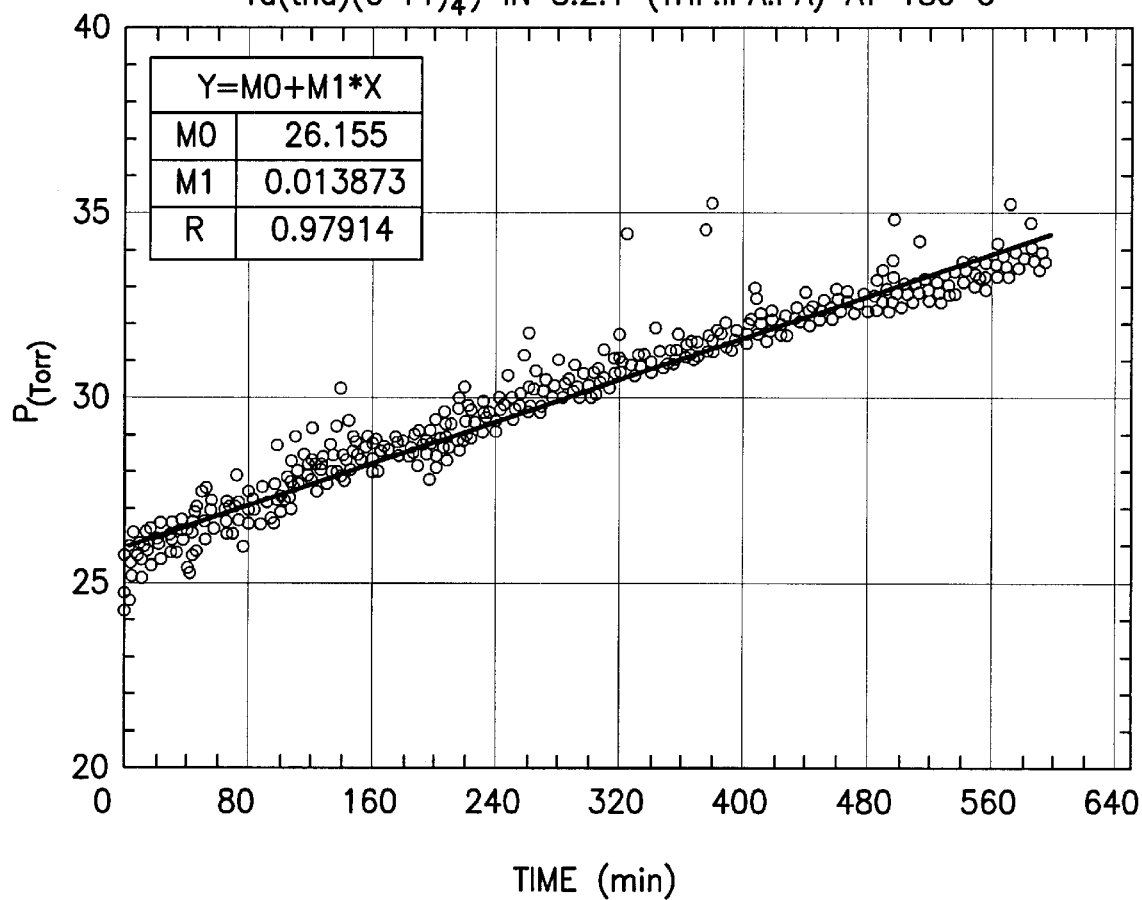
FIG. 1 is a plot of upstream pressure, in Torr, as a function of time, in minutes, for a liquid delivery chemical vapor deposition system employed for vaporization of the precursor solution at 180° C. and deposition of strontium bismuth tantalate, utilizing β-diketonate precursors for strontium, bismuth and tantalum, in a 8:2:1 solvent composition of tetrahydrofuran:isopropanol:polyamine.

The disclosures of the following U.S. Patent Applications are hereby incorporated herein in their entireties: U.S. patent application Ser. No. 09/224,614 filed Dec. 31, 1998 and now U.S. Pat. No. 6,111,124, U.S. patent application Ser. No. 09/185,374 filed Nov. 3, 1998 and now U.S. Pat. No. 6,214,105, U.S. patent application Ser. No. 08/975,372 filed Nov. 20, 1997 and now U.S. Pat. No. 5,916,359; U.S. patent application Ser. No. 08/484,654 filed Jun. 7, 1995 and now U.S. Pat. No. 6,110,529; U.S. patent application Ser. No. 08/414,504 filed Mar. 31, 1995 and now U.S. Pat. No. 5,820,664; U.S. patent application Ser. No. 8/960,915 filed Oct. 30, 1997 and now U.S. Pat. No. 5,859,274; and U.S. patent application Ser. No. 08/975,087; filed Nov. 20, 1997.

The present invention is based on the discovery of solvent compositions which are advantageously used for liquid delivery chemical vapor deposition of metal organic precursors such as metal β-diketonate precursors, e.g., of Group II and other metals. Such solvent compositions have been found highly advantageous in carrying out deposition of metals from such β-diketonate precursors, including β-diketonate-based complexes of metals such as strontium, bismuth, tantalum, and the like.

One class of compositions of the present invention comprises a mixture of solvent species A, B and C in the proportion A:B:C wherein A is from about 1 to about 10 parts by volume of the solution (A+B+C), B is from about 0 to about 6 parts by volume of the solution, and C is present in an amount from zero up to about 4 parts by volume, wherein such parts by volume are based on the total volume of the solution, and wherein A is a C$_6$–C$_8$ alkane, B is a C$_8$–C$_{12}$ alkane, A and B are different from one another, and C is a Lewis base ligand selected from the group consisting of glyme-based solvents (glyme, diglyme, triglyme, tetraglyme, etc.), ethers, amines, diamines, polyamines aryls and aryl amines. A highly preferred composition according to the invention includes octane as the solvent species A and decane as the solvent species B, with C being either or a diamine or polyamine, in a 5:4:1 ratio of the respective solvent species A, B and C.

In a particularly preferred aspect of such compositions of the invention, a 5:4:1 solvent mixture of octane: decane: polyamine is utilized as a solvent species for each of the strontium, bismuth and tantalum β-diketonate precursors for liquid delivery chemical vapor deposition of SrBi$_2$Ta$_2$O$_9$.

In another particularly preferred aspect of such compositions of the invention, a 9:1 solvent mixture of octane:polyamine is utilized as a solvent species for each of the strontium, bismuth and tantalum β-diketonate precursors for liquid delivery chemical vapor deposition of SrBi$_2$Ta$_2$O$_9$.

The solvent compositions of the invention permit low-pressure volatilization of the β-diketonate precursors, and afford good transport and minimal residue in the vaporization and chemical vapor deposition process.

When C in the A:B:C solvent mixture is a polyamine, the polyamine component of the solvent composition may be any suitable polyamine. Examples include N,N,N',N'-tetramethylethylenediamine (tmeda), N,N,N',N'',N''-pentamethyl diethylenetriamine (pmdeta), N,N,N',N'',N''', N'''-hexamethyHriethylenetetramine (hmteta), etc.

The metal β-diketonate precursors with which the solvent composition of the invention may be employed include β-diketonato compositions whose metal constituent may be any suitable metal, as for example strontium, bismuth, tantalum, niobium, copper, gold, palladium, lead, calcium, barium, iron, aluminum, scandium, yttrium, titanium, zirconium, tungsten, molybdenum and lanthanide metals such as Ce, La, Pr, Ho, Eu, Yb, etc. The β-diketonate ligand may be any suitable species, as for example a β-diketonate ligand selected from the group consisting of:

2,2,6,6-tetramethyl-3,5-heptanedionato (thd);

1,1,1-trifluoro-2,4-pentanedioiato (tfac);

1,1,1,5,5,5-hexafluoro-2,4-pentanedionato (hfac);

6,6,7,7,8,8,8-heptafluoro-2,2-dimethyl-3,5-octanedionato (hfod);

2,2,7-trimethyl-3,5-octanedionato (tod)

1,1,1,5,5,6,6,7,7,7-decafluoro-2,4-heptanedionato (dfhd); and 1,1,1-trifluoro-6-methyl-2,4-heptanedionato (tfmhd).

The solvent composition of the present invention has particular utility for the deposition of bismuth-containing thin films, using bismuth precursors such as polyamine adducted anhydrous mononuclear tris(2,2,6,6-tetramethyl-3, 5-heptanedionato)bismuth and polyamine-adducted Sr(thd)$_2$. Such metal β-diketonate compounds may be readily employed in the solvent compositions of the invention to prepare superior bismuth-containing thin films, such as SrBi$_2$Ta$_2$O$_9$.

In another class of solvent compositions, the solvent medium may comprise an alkane solvent medium, comprising one or more hydrocarbon solvent species. Such alkane solvent medium enables a process for forming a film of SrBi$_2$Ta$_2$O$_9$ (SBT) on a substrate, in applications such as the formation of ferroelectric microelectronic device structures, wherein the precursors Sr(thd)$_2$(pmdeta), Ta(OiPr)$_4$(thd) and Bi(thd)$_3$(pmdeta) are employed in a solvent medium comprising one or more alkanes and a Lewis base ligand. The alkanes may be of any suitable type and carbon number, e.g., the solvent medium may comprise one or more compatible solvent species selected from C$_1$–C$_{10}$ alkanes. The Lewis base ligand of the solvent system is pmdeta. The metal organic compound(s) may be formulated in the solvent to form a precursor solution or suspension by simple mixing of the compound(s) with the solvent medium, followed by agitation, gentle heating, sonication dispersal, etc., as necessary or desirable in a specific end use application to place the compound(s) in the solvent medium employed.

The alkane solvent medium may for example comprise solvent species such as butane, pentane, hexane, heptane, octane, nonane, decane, etc., and solvent compositions of different alkanes may be employed to adjust the boiling point of the overall solvent medium by appropriate proportion of the constituent solvents having different individual boiling points. The resulting precursor composition is storage stable at room temperature for at least several weeks, during which time it remains clear and shows no precipitation or discoloration. By selectively mixing alkane solvent components having different boiling points, it is possible to selectively adjust the overall boiling point of the solvent composition to accommodate boiling point as well as solubility requirements.

Thus, by mixing different alkanes having different boiling points, the solvent of the desired boiling point can be selected. Furthermore, mixing two or more alkanes is also useful to achieve a desired boiling point. The capability of adjusting the boiling point is advantageous as it enables reliable operation, since the solvent can be adjusted to accommodate the evaporation characteristics of a specific precursor.

The alkane solvent compositions of the invention have the further advantage that degenerate ligand exchange reactions are typically slow in non-polar solvent media with the result that the precursor compositions including alkane solvent media will be very stable in high temperature vaporization conditions in MOCVD operations. Additionally, alkanes are relatively inert to the metal organic precursor compound(s), in contrast to solvent media such as alcohols, which can act in a reducing manner, delivering electrons to reduce the metal ion of the precursor compound(s) to the corresponding metal, as occurred with $Bi(thd)_3$ in alcoholic solvent media in the hot vaporization zone of the CVD process system (see discussion in the Background section hereof).

Alkane-based solvent compositions thus have the following advantages:

they show good stability and solubility for precursors containing β-diketonate ligands such as thd, as well as for precursor compound(s) containing alkoxide, aryl, and/or alkyl functionality;

their solutions are stable with time, enabling stable storage, handling and delivery of the precursor solutions to the reactor;

the boiling point of the solvent can readily be adjusted to a desired value by appropriate mixing of different alkane solvent species; and the ligand exchange process is slow in such solvent media, and therefore the solutions will be stable in elevated temperature conditions such as are encountered in the vaporization zone of the MOCVD process system, with a corresponding decrease in premature decomposition of the precursors relative to other solvent media permitting faster and more extensive ligand reactions.

The solvent-based precursor compositions of the invention may be employed to form a wide variety of thin film articles and device structures, including microelectronic device structures such as memory structures (e.g., FeRAMs).

The invention therefore contemplates precursor compositions for MOCVD of a metal-containing film on a substrate, wherein the precursor composition includes a solvent medium comprising one or more alkanes, having dissolved therein one or more compatible metal organic compound(s). Such compound(s) may for example be β-diketonate compounds or complexes, compound(s) including alkoxide ligands, compound(s) including (non-polar) alkyl and/or aryl groups at their outer (molecular) surface, or compound(s) including other ligand coordination species and specific metal constituents.

In one embodiment, such compound(s) may be selected from the group consisting of $Sr(thd)_2$(tetraglyme), $Sr(thd)_2$(polyamine), $Ba(thd)_2$(tetraglyme), $Ba(thd)_2$(polyamine), $Ta(OiPr)_4(thd)$, $Ti(OiPr)_2(thd)_2$, $Zr(OiPr)_2(thd)_2$, $[Zr(OiPr)_3(thd)_2]_2$, $Zr(thd)_4$, $Bi(thd)_3$, $Bi(thd)$(polyamine), $Pb(thd)_2$, $Pb(thd)_2$(tmeda), $Pb(thd)_2$(pmdeta), $Pt(thd)_2$, $Pt(hfac)_2$, (methylcyclopentadienyl)$Pt(Me)_3$, $(MeCN)_2PtMe_2$, $Pd(allyl)_2$, $Pd(hfac)_2$, $Me_2Au(hfac)$, $MeAu(PMe_3)$, $Cu(hfac)_2$, $(COD)Cu(hfac)$, $(DMCOD)Cu(hfac)$, $(MHY)Cu(hfac)$, $(Me_3P)CuO^tBu$, $Ta(OR)_5$ and $Ti(OR)_4$. In such formulae, Me=methyl, tmeda=N,N,N',N'-tetramethylethylenediamine, pmdeta=N,N,N'N'N''-pentamethyldiethylenetriamine, COD=cyclooctadiene, thd=2,2,6,6-tetramethyl-3,5-heptanedionato, hfac=1,1,1,5,5,5-hexafluoro-2,4-pentanedionato, $R=C_1–C_8$ alkyl (branched or straight chain), and $^tBu$=tert-butyl. Other compounds and coordinated complexes can be employed, e.g., other β-diketonate ligands including, without limitation, 1,1,1-trifluoro-2,4-pentanedionato, denoted tfac; 6,6,7,7,8,8,8-heptafluoro-2,2-dimethyl-3,5-octanedionato, denoted fod; 2,2,7-trimethyl-3,5-octanedionato, denoted tod; 1,1,1,5,5,6,6,7,7,7-decafluoro-2,4-heptanedionato, denoted dfhd; and 1,1,1-trifluoro-6-methyl-2,4-heptanedionato, denoted tfmhd.

In one preferred embodiment such compounds may be selected from the group consisting of $Sr(β\text{-diketonate})_2(L)_m$, $Ta(alkoxide)_4(β\text{-diketonate})$ and $Bi(β\text{-diketonate})_3(L)_m$, wherein the β-diketonate is selected from the group consisting of:

2,2,6,6-tetramethyl-3,5-heptanedionato;

1,1,1-trifluoro-2,4-pentanedionato;

1,1,1,5,5,5-hexafluoro-2,4-pentanedionato;

6,6,7,7,8,8,8-heptafluoro-2,2-dimethyl-3,5-octanedionato;

2,2,7-trimethyl-3,5-octanedionato;

1,1,1,5,5,6,6,7,7,7-decafluoro-2,4-heptanedionato; and 1,1,1-trifluoro-6-methyl-2,4-heptanedionato;

the alkoxide ligand is selected from the group consisting of $C_1–C_8$ alkyls, L is a Lewis base ligand and m is a value between ½ and 5 and more preferably m is one.

The Lewis base ligands of the present invention may be selected from the group consisting of: amines, ethers, glymes, aryls and aryl amines, more preferably selected from the group consisting of: $NH_3$, primary amines, secondary amines, tertiary amines, polyamines, monoglymes, diglymes, triglymes, tetraglymes, aliphatic ethers, polyethers, and cyclic ethers and most preferably selected from the group consisting of tetrahydrofuran, pyridine, toluene, N,N,N'N'-tetramethylethylenediamine (tmeda) and N,N,N'N',N''-pentamethyldiethylenetriamine (pmdeta).

In a preferred embodiment the precursor compositions of the present invention may comprise a bismuth Lewis base adduct precursor having the formula $Bi(β\text{-diketonate})_3(L)_m$, dissolved in a solvent composition comprising one or more alkanes and a Lewis base ligand, wherein L is a Lewis base ligand and m is a value between ½ and 5 and the Lewis base ligand of the precursor component and the Lewis base ligand of the solvent composition are the same.

In a more preferred embodiment the metal organic precursors of the present invention are selected from the group consisting of $Sr(thd)_2$(pmdeta), $Ta(OiPr)_4(thd)$ and $Bi(thd)_3$(pmdeta) and the metal organic compounds are dissolved in a solvent medium comprising octane, decane and pmdeta in a 5:4:1 ratio.

In a most preferred embodiment the metal organic precursors of the present invention are selected from the group consisting of $Sr(thd)_2(pmdeta)$, $Ta(OiPr)_4(thd)$ and $Bi(thd)_3$ (pmdeta) and the metal organic compounds are dissolved in a solvent medium comprising octane, and pmdeta in a 9:1 ratio.

The alkane solvent compositions of the invention may be usefully employed for a variety of metal organic compound (s) having the metal species coordinated with one or more alkoxide ligands, such as for example ethoxide groups, isopropoxide groups, etc., and/or metal organic compound (s) having unpolar alkyl and/or aryl groups at their outer molecular surface, including, without limitation, carboxylates, e.g., Bi pivalate, alkoxides, e.g., Bi pentoxide, Bi amides, e.g., $Bi(NMe_2)_3$, alkyls, e.g., triethylaluminum and $Al(OiPr)_3$, and aryls, e.g., triphenylbismuth.

Precursor solutions therefore are readily formed using the alkane solvent compositions of the invention. The resulting solution is then vaporized to form a precursor vapor, which can be introduced into a deposition chamber to deposit a metal-containing film on a substrate, e.g., a wafer, that is contacted with the precursor vapor. Multiple precursors may be utilized in a desired ratio and provided in a solution in a single reservoir for delivery to the liquid vaporizer and subsequently the reactor (deposition chamber). Alternatively, separate precursor solutions may be provided in separate reservoirs, and be subsequently mixed in an appropriate ratio to provide a combined precursor liquid solution for subsequent vaporization and deposition, or the separate precursor solutions may each be separately vaporized and the resulting vapors then mixed in a desired ratio to provide a combined precursor vapor which then is flowed to the deposition chamber for contacting with the substrate.

The present invention provides a solvent composition for precursors useful to produce CVD films. The solvent may comprise a compound selected from the group comprising alkanes. Alkanes in one embodiment comprise butane, hexane, heptane, octane or decane. In one embodiment, the solvent composition comprises hexane. A solvent composition comprising more than one alkane compound is also useful in the broad practice of the present invention.

In one embodiment of the invention, the solvent is used to dissolve a CVD precursor selected from the group comprising metal β-diketonates. CVD precursors comprising an alkoxide ligand or a thd ligand can also be used in the alkane solvent composition, e.g., metal β-diketonates including an alkoxide ligand or a thd ligand. A CVD precursor including an alkyl group or an aryl group at its outer molecular surface, e.g., a non-polar group of such type, can also be utilized in the alkane solvent composition. Other precursors such as $Pt(thd)_2$, $Pt(hfac)_2$, $(MeCp)PtMe_3$, $(MeCN)_2PtMe_2$, $Pd(allyl)_2$, $Pd(hfac)_2$, $Me_2Au(hfac)$, $MeAu(PMe_3)$, $Cu(hfac)_2$, $(COD)Cu(hfac)$, $(Me_3P)CuO^tBu$ are soluble in alkanes, and usefully employed in the practice of the invention.

In another embodiment, precursors with alkoxide ligands include $Ta(thd)(OiPr)_4$, $Ta(OEt)_5$, $Ta(OiPr)_4$, $Ti(OEt)_5$, $Ti(OEt)_4$, Bi pentoxide, $Ti(OiPr)_4$, and $Zr(OiPr)_4$. Other alkoxide precursors are also useful.

In yet another embodiment, the CVD precursors comprise precursors having non-polar alkyl groups at their outer molecular surface. Precursors with non-polar alkyl groups in their outer molecular surface include precursors comprising carboxylate compounds, amide compounds, alkoxide compounds, and aryl compounds. Amidecontaining precursors include, for example, $Bi(NMe_2)_3$. Alkyl-containing precursors include, for example, $AlEt_3$ and $Al(OiPr)_3$. Aryl-containing precursors include for example $BiPh_3$. Other precursors such as $Pt(thd)_2$, $Pt(hfac)_2$, $(MeCp)PtMe_3$, $(MeCN)_2PtMe_2$, $Pd(allyl)_2$, $Pd(hfac)_2$, $Me_2Au(hfac)$, $MeAu(PMe_3)$, $Cu(hfac)_2$, $(COD)Cu(hfac)$, $(Me_3P)CuO^tBu$ are also useful CVD precursors.

The CVD precursor compositions of the invention are useful in depositing metal-containing films. In one embodiment, the metal-containing film comprises metal oxide ceramics. In another embodiment, the metal oxide ceramic comprises or is capable of comprising ferroelectric properties. Non-ferroelectric metal oxide ceramics are also useful. In one embodiment, the metal oxide ceramic comprises paraelectric characteristics. Metal-containing films that comprise a high dielectric constant are also useful.

A ferroelectric metal oxide ceramic may be used for example in ferroelectric transistors or non-volatile ferroelectric memory cells for non-volatile ferroelectric memory ICs. Non-volatile ferroelectric memory cells and ferroelectric ICs are described for example in U.S. patent application Ser. No. 08/974,779, now U.S. Pat. No. 5,923,970, for "METHOD OF FABRICATING A FERROELECTRIC CAPACITOR WITH A GRADED BARRIER LAYER," the disclosure of which is hereby incorporated herein by reference in its entirety.

The metal oxide ceramic may for example be deposited on a substrate by CVD, e.g., a low temperature CVD process, and/or with amorphous deposition of the metal oxide ceramic by CVD, as for example are described in U.S. patent application Ser. No. 08/975,087 for "LOW TEMPERATURE CHEMICAL VAPOR DEPOSITION PROCESS FOR FORMING BISMUTH-CONTAINING CERAMIC FILMS USEFUL IN FERROELECTRIC MEMORY DEVICES," the disclosure of which is hereby incorporated herein by reference in its entirety.

The substrate may be processed to include, for example, a gate oxide of a ferroelectric transistor. In other cases, the substrate may be processed to include a bottom electrode of a ferroelectric capacitor. The bottom electrode is patterned on an interlevel dielectric. The substrate may also be processed to include other types of materials. Circuit components of an IC, such as transistors, may also be included on the substrate.

In one embodiment, the metal oxide ceramic comprises or is capable of comprising ferroelectric properties. The metal oxide ceramic comprises Bi-based oxide ceramics. The Bi based oxide is generally expressed by $ABi_2B_2O_9$, where A comprises a 2-valent cation and B comprises a 5-valent cation. In one embodiment, B is equal to one or more elements selected from Sr, Ba, Pb, and Ca. A, in one embodiment, is equal to one or more elements selected from Ta and Nb.

In one embodiment, the Bi-based oxide ceramic comprises Sr. A Bi-based oxide comprising Sr and Ta is also useful. Preferably, the Bi-oxide comprises $SrBi_2Ta_2O_9$.

Derivatives of SBT are also useful. In one embodiment, the SBT derivative comprises Bi and Ta. In another embodiment, the SBT derivative comprises Bi and Sr. In yet another embodiment, the SBT derivative comprises Bi, Sr, and Ta. SBT derivatives include, for example, $SrBi_2Ta_{2-x}Nb_xO_9$ ($0<x<2$), $SrBi_2Nb_2O_9$, $Sr_{1-x}Ba_xBi_2Ta_{2-y}Nb_yO_9$ ($0 \leq x \leq 1$, $0 \leq y \leq 2$), $Sr_{1-x}Ca_xBi_2Ta_{2-y}Nb_yO_9$ ($0 \leq x \leq 1$, $0 \leq y \leq 2$), $Sr_{1-x}Pb_xBi_2Ta_{2-y}Nb_yO_9$ ($0 \leq x \leq 1$, $0 \leq y \leq 2$), or $Sr_{1-x-y-z}Ba_xCa_yPb_zBi_3Ta_{2-p}Nb_pO_9$ ($0 \leq x < 1$, $0 \leq y \leq 1$, $0 \leq z \leq 1$, $0 \leq p \leq 2$).

In yet another embodiment, substituting or doping at least one element of the Bi-based oxide with a metal of the lanthanide series is also useful.

In another embodiment, the Bi-based oxide ceramic comprises an Aurivillius phase expressed generally by $(Bi_2O_2)^{2+}(A_{m-1}B_mO_{3m+1})^{2-}$, wherein $A=Bi^{3+},L^{3+},L^{2+},Ca^{2+}, Sr^{2+},Ba^{2+},Pb^{2+},Na^+, B=Fe^{3+},Al^{3+},Sc^{3+}, Y^{3+},L^{3+},L^{4+},Ti^{4+}, Nb^{5+},Ta^{5+},W^{6+}$ and $Mo^{6+}$, wherein L is a lanthanide series metal ($Ce^{4+},La^{3+},Pr^+,Ho^{3+},Eu^{2+},Yb^{2+}$ etc.) and m=1,2,3,4 or 5.

In yet another embodiment, metal oxide ceramic including lead-based oxide ceramics, such as lead zirconium titanate (PZT), lead lanthanum titanate (PLT) and lithium niobium oxide ($LiNbO_2$) are also useful. Also, non-ferroelectric metal oxide ceramics are useful. In one embodiment, a metal ceramic oxide comprises a superconductor material such as a Bi-based high temperature superconductor material. Bi-based high temperature superconductor layers are referred to, for example, as "BSCCO" or "bissco." BSCCO are described in, for example, Rees, "CVD of Nonmetals" (1996) ISBN 3-527-29295-0, the disclosure of which is hereby incorporated herein by reference for all purposes. Typical compositions of BSCCO include, for example, $Bi_2Sr_2CaCu_2O_x$ or $(Pb, Bi)_2Sr_2CaCu_2O_x$. Other compositions of BSCCO include, for example, $Bi_2Sr_2CuO_x$ and $Bi_2Sr_2CaCu_2O_x$.

Features and advantages of the present invention are more fully shown with respect to the following non-limiting example, wherein all parts and percentages are by weight, unless otherwise expressly stated.

EXAMPLE

A solution containing 7 atomic percent $Sr(thd)_2$ (pentamethyldiethylenetriamine), 55 atomic percent $Bi(thd)_3$ and 38 atomic percent $Ta(OiPr)_4(thd)$, wherein thd=2,2,6,6tetramethyl-3,5-heptanedionato, in a solvent composition of 5:4:1 octane:decane:pentamethyldiethylenetriamine is metered to the liquid delivery chemical vapor deposition system where the precursor solution is flash vaporized at 190° C. and then carried to the CVD chamber in 400 sccm argon.

The precursor vapor is mixed with 1100 sccm oxygen and then additional 100 sccm argon for a combined for a 7:3 oxygen:argon ratio, and is passed through a showerhead disperser to the chemical vapor deposition chamber which is maintained at 1 Torr. Decomposition occurs on a substrate heated to a surface temperature of 385° C. The substrate is a 0.5 micron linewidth $SiO_2$ (TEOS) structure covered with platinum. The SBT film produced on the substrate is highly conformal, exhibiting a minimum SBT thickness which is greater than 90% of the maximum thickness, consistent with the device requirements for microelectronic fabrication. The low temperature and amorphous character of the deposition contribute to the conformal coating of the deposited film. Under these conditions, the composition varies less than 0.5% relative (which is the precision of the x-ray fluorescence method employed).

FIG. 1 is a plot of upstream pressure, in Torr, as a function of time, in minutes, for a liquid delivery system employed for deposition of strontium bismuth tantalate, with vaporization of the precursor solution at 180° C., and utilizing β-diketonate precursors for strontium, bismuth and tantalum, in a 8:2:1 solvent composition of tetrahydrofuran:isopropanol:polyamine. Such solvent composition is typical of the solvent compositions heretofore used in the art for precursors such as metal β-diketonates and adducts thereof.

Figure 2:
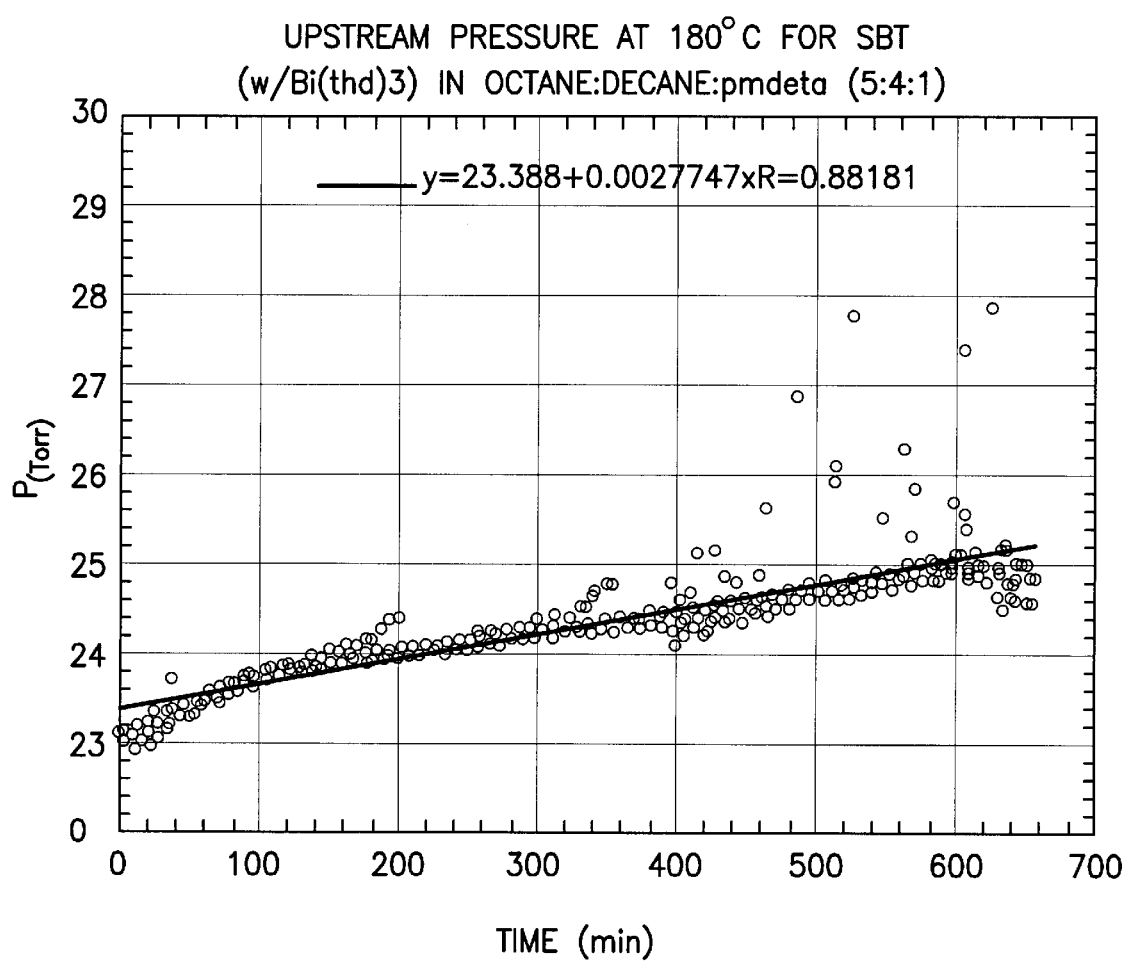
FIG. 2 is a plot of upstream pressure, in Torr, as a function of time, in minutes, for a liquid delivery chemical vapor deposition system employed for deposition of strontium bismuth tantalate following precursor solution vaporization at 180° C., utilizing β-diketonate precursors for strontium, bismuth and tantalum, in a solvent composition according to the invention comprising 5:4:1 octane:decane:polyamine.

FIG. 2 shows upstream pressure in a liquid delivery system employed for vaporization of metal organic precursors in a solvent composition of the present invention, 5:4:1 octane:decane:pentamethyldiethylenetriamine. The precursor components of such precursor solution are $Sr(thd)_2$ (pentamethyldiethylenetriamine), $Bi(thd)_3$ and $Ta(OiPr)_4$ (thd) where thd=2,2,6,6-tetramethyl-3,5-heptanedionato, wherein the bismuth reagent is of anhydrous mononuclear form.

The plot of FIG. 2 shows the upstream pressure in Torr as a function of time in minutes for vaporization of the precursor solution at 180° C. As shown, the upstream pressure is highly uniform over the time frame of the process, indicating good vaporization and transport properties of the precursors in such solvent composition with concomitant low levels of residue (significant levels of residue being indicative of clogging which significantly increases upstream pressure).

The steep increase in pressure shown in the curve for FIG. 1 is indicative of decomposition of the precursor resulting in clogging of the liquid delivery system. As a consequence of such clogging, the liquid delivery system fails to deliver the precursor in the desired amount and at the desired rate to the downstream chemical vapor deposition chamber, and thereby lowers the overall process efficiency.

The plots of FIGS. 1 and 2 therefore show the superior solvent efficiency of the solvent composition of the present invention.

EXAMPLE II

A solution containing 7 atomic percent $Sr(thd)_2$ (pentamethyldiethylenetriamine), 55 atomic percent $Bi(thd)_3$ and 38 atomic percent $Ta(OiPr)_4(thd)$, wherein thd=2,2,6,6-tetramethyl-3,5-heptanedionato, in a solvent composition of 9:1 octane:pentamethyl-diethylenetriamine is metered to the liquid delivery chemical vapor deposition system where the precursor solution is flash vaporized at 190° C. and then carried to the CVD chamber in 400 sccm argon.

While the invention has been illustratively described with respect to particular features, aspects and embodiments herein, it will be appreciated that the utility of the invention is not thus limited, and other variations, modifications and embodiments will readily suggest themselves to those skilled in the art. Accordingly, the invention is to be broadly construed, consistent with the claims hereafter set forth.

What is claimed is:

1. A precursor composition for MOCVD of a metal-containing film on a substrate, wherein the precursor composition includes a solvent medium comprising one or more alkanes having dissolved therein one or more compatible metal organic compound(s) wherein at least one metalorganic compound is a bismuth Lewis base adduct of the formula:

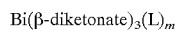

Bi(β-diketonate)$_3$(L)$_m$ wherein L is a Lewis base ligand selected from the group consisting of: amines, ethers, glymes, aryls and aryl amines and m is a value from ½ to 5.

2. The precursor composition according to claim 1, wherein the β-diketonate ligand is selected from the group consisting of:
2,2,6,6-tetramethyl-3,5-heptanedionato;
1,1,1-trifluoro-2,4-pentanedionato;
1,1,1,5,5,5-hexafluoro-2,4-pentanedionato;
6,6,7,7,8,8,8-heptafluoro-2,2-dimethyl-3,5-octanedionato;

2,2,7-trimethyl-3,5-octanedionato;
1,1,1,5,5,6,6,7,7,7-decafluoro-2,4-heptanedionato; and
1,1,1-trifluoro-6-methyl-2,4-heptanedionato.

3. The precursor composition according to claim 1, wherein the Lewis base ligand is selected from the group consisting of: NH3, primary amines, secondary amines, tertiary amines and polyamines.

4. The precursor composition according to claim 1, wherein the Lewis base ligand is selected from the group consisting of: monoglymes, diglymes, triglymes, tetraglymes, aliphatic ethers, polyethers, and cyclic ethers.

5. The precursor composition according to claim 1, wherein the Lewis base ligand is tetrahydrofuran.

6. The precursor composition according to claim 1, wherein the Lewis base ligand is selected from the group consisting of toluene and pyridine.

7. The precursor composition according to claim 1, wherein the Lewis base ligand is selected from the group consisting of: N,N,N',N'-tetramethylethylenediamine and N,N,N',N',N''-pentamethyldiethylenetriamine.

8. The precursor composition according to claim 1, wherein the metal organic compound(s) further comprise $Sr(\beta\text{-diketonate})(L)_m$ and $Ta(alkoxide)_4(\beta\text{-diketonate})$.

9. The precursor composition according to claim 1, wherein the bismuth Lewis base adduct is $Bi(thd)_3(pmdeta)$.

10. The precursor composition according to claim 9 wherein the metal organic compound(s) further comprise $Sr(thd)_2(pmdeta)$ and $Ta(OiPr)_4(thd)$.

11. The precursor composition according to claim 10, wherein the solvent medium comprises octane, decane and pmdeta.

12. The precursor composition according to claim 10, wherein the solvent medium comprises octane, decane and pmdeta in a 5:4:1 ratio.

13. The precursor composition according to claim 1 wherein the bismuth Lewis base adduct is $Bi(thd)_3(tmeda)$.

14. The precursor composition according to claim 13, wherein the solvent medium comprises octane, decane and tmeda.

15. The precursor composition according to claim 13, wherein the solvent medium comprises octane, decane and pmdeta in a 5:4:1 ratio.

16. The precursor composition according to claim 1, wherein the solvent medium comprises at least one solvent species selected from the group consisting of $C_1$–$C_{10}$ alkanes.

17. The precursor composition according to claim 1, wherein the solvent medium comprises at least one solvent species selected from the group consisting of pentane, octane, hexane, and decane.

18. The precursor composition according to claim 1, wherein the solvent medium comprises octane, decane and pmdeta.

19. The precursor composition according to claim 1, wherein the solvent medium comprises octane, decane and pmdeta in a 5:4:1 ratio.

20. The precursor composition according to claim 1, wherein the solvent medium comprises octane and pmdeta.

21. The precursor composition according to claim 1 wherein the solvent medium comprises octane and pmdeta in a 9:1 ratio.

22. The precursor composition according to claim 1, further comprising a second metal organic compound.

23. The precursor composition according to claim 22, wherein the second metal organic compound comprises one or more alkoxide ligands.

24. The precursor composition according to claim 22 wherein the second metal organic compound comprises at least one of ethoxide groups and isopropoxide groups.

25. The precursor composition according to claim 22, wherein the second metal organic compound comprises one or more alkyl and/or aryl groups at their outer molecular.

26. The precursor composition according to claim 22, wherein the second metal organic compound comprises one or more functional groups selected from the group consisting of carboxylates, alkoxides, amides, alkyls, and aryls.

* * * * *